United States Patent [19]

Partika

[11] Patent Number: 5,383,466

[45] Date of Patent: Jan. 24, 1995

[54] INSTRUMENT HAVING ENHANCED ULTRASOUND VISIBILITY

[75] Inventor: Lawrence Partika, Bridgewater, N.J.

[73] Assignee: Becton, Dickinson and Company, Franklin Lakes, N.J.

[21] Appl. No.: 62,917

[22] Filed: May 14, 1993

[51] Int. Cl.⁶ .................................. A61B 10/00
[52] U.S. Cl. ........................................... 128/662.03
[58] Field of Search ............... 128/662.02, 662.03, 128/662.05, 749, 751-754

[56] References Cited

U.S. PATENT DOCUMENTS

| | | | |
|---|---|---|---|
| 4,401,124 | 8/1983 | Guess et al. | 128/660 |
| 4,582,061 | 4/1986 | Fry | 128/329 |
| 4,805,628 | 2/1989 | Fry et al. | 128/662.02 |
| 4,869,259 | 9/1989 | Elkins | 128/662.02 |
| 5,201,314 | 4/1993 | Bosley et al. | 128/662.02 |

FOREIGN PATENT DOCUMENTS 2425724 11/1975 Germany .

*Primary Examiner*—Max Hindenburg
*Attorney, Agent, or Firm*—Vincent A. Castiglione

[57] ABSTRACT

A medical instrument is provided with enhanced ultrasonic visibility. The medical instrument includes an elongate probe or needle for insertion into a patient. Selected locations along the instrument are provided with deposits of a material exhibiting a high degree of ultrasonic reflectivity. The material includes a matrix of gas bubbles contained in a polymeric material. The gas bubbles exhibit high reflectivity of ultrasonar energy.

20 Claims, 4 Drawing Sheets

INSTRUMENT HAVING ENHANCED ULTRASOUND VISIBILITY

FIELD OF THE INVENTION

The subject invention relates to a medical instrument used during ultrasound imaging procedures and more particularly to an instrument having at least selected regions that are highly reflective of ultrasound energy.

DESCRIPTION OF THE PRIOR ART

The prior art ultrasound imaging apparatus includes a transducer that is operative to both emit and receive ultrasound energy. The transducer of the prior art ultrasound imaging apparatus typically is held against the skin of the patient and emits ultrasound energy into the patient. A portion of the emitted ultrasound energy is reflected back from body structures and is received by the transducer. The transducer converts the reflected ultrasound energy signals into electric signals which are transmitted to a processor of the prior art apparatus. The prior art apparatus further includes a black and white video monitor which displays a real time video image of the body parts from which the sound waves have been reflected.

Medical procedures often require diagnosis of tissue samples from regions that are being ultrasonically imaged. Tissue samples usually are obtained with long needles that are placed percutaneously into the area of interest. The doctor or medical technician will attempt to observe the needle on the video screen of the ultrasonic imaging apparatus to ensure that a tissue sample from the proper location is obtained and to be certain that the sharply pointed prior art needle cannula causes no damage. For example, the prior art combination of an ultrasonic imaging apparatus and a sharply pointed needle cannula is used for amniocentesis where a sample of amniotic fluid must be obtained without contacting the fetus.

Medical procedures that utilize ultrasonic imaging are complicated by the poor sonar reflectivity of the prior art metallic instruments used during the procedures. More particularly, body tissue is reflective of sonar energy, and will appear fairly clearly on the black and white video screen of the ultrasonic imaging apparatus. However, a cylindrical metallic instrument, such as a biopsy needle, tends to disburse the ultrasonic energy impinging thereon, and hence a standard cylindrical metallic instrument is substantially invisible on the monitor of the ultrasonic imaging apparatus. FIG. 1 provides a schematic example of this problem. In particular, a prior art ultrasonic transducer 100 in FIG. 1 directs ultrasonic energy toward a prior art biopsy needle 102. However, the arrows in FIG. 1 show that virtually all of the ultrasonic energy will be reflected away from the prior art transducer, and hence will not be detected. A significant amount of ultrasonic energy will be reflected only when the emitted energy is aligned approximately orthogonally to the axis of the prior art biopsy needle 102.

The ultrasonic visibility of prior art biopsy needles can be enhanced as shown in FIG. 2 by providing annular grooves 104 at selected locations around the outer circumference of prior art biopsy needle 106. The grooves are intended to define surfaces that are more likely to reflect sonar energy toward the transducer 100 than the smooth cylindrical surface of biopsy needle 102 in FIG. 1. The annular grooves are at a selected spacing from the tip of the prior art biopsy needle so that the location of the tip can be positively determined. Additionally, a plurality of annular grooves may be spaced along the length of the prior art biopsy needle so that the alignment of the prior art biopsy needle can be determined from the ultrasonically generated image on the video monitor.

The annularly grooved prior art biopsy needles improve ultrasonic visibility as compared to biopsy needles with smooth exteriors. However, even the grooved prior art biopsy needles tend to widely disburse most ultrasonic energy. The provision of grooves sufficiently large to reflect a significant portion of the ultrasonic energy imposes a cost penalty on the needle manufacturing process which must form these grooves.

Some prior art diagnostic procedures involve ultrasonic imaging of the liver independent of or prior to any need to obtain a biopsy from the liver. Diagnostic procedures have been developed to enhance the ultrasonic visibility of the liver. These procedures involve injecting a substance containing microscopic particles of reflecting substance intravenously. The substance effectively defines a matrix of microspheres which entrain a gaseous material. The microspheres eventually dissolve and the entrained gas disperses into and through bodily tissue. However, a significant number of the microspheres will remain intact sufficiently long to travel to and accumulate in the liver. The small air bubbles defined by the microspheres are highly reflective of ultrasonic energy and hence improve the ultrasonic visibility of the liver. Eventually, all of the entrained gases will be absorbed into bodily tissue.

SUMMARY OF THE INVENTION

The subject invention is directed to a medical instrument that can be inserted into a patient as part of a procedure involving ultrasonic imaging. The instrument is provided with at least one ultrasonic reflector defined by a layer of material having a plurality of small cavities contained therein. The cavities or bubbles contain air or other gas and this material, on the medical instrument, is a good reflector of ultrasonic energy. Thus, the small entrained bubbles overcome the relative lack of sonic reflectivity of the underlying metal from which the medical instrument is usually made.

Each ultrasonic reflector on the instrument may define a thin polymer matrix applied to at least one specified location on the instrument. The polymer may define a foam that is cured to a hardened condition and permanently secured to at least one location on the instrument. Secure permanent retention of the ultrasonic reflector on the instrument may be enhanced by initially roughening a local region on the medical instrument or by forming an undercut on the medical instrument into which the ultrasonic reflector may be deposited.

Preferably, the ultrasonic reflector defines at least one annular band extending around the medical instrument. Additionally, at least one ultrasonic reflector is disposed at a known distance from the extreme distal tip of the medical instrument so that the location of the tip can be accurately determined on the ultrasonic image. Preferably, a plurality of the sonic reflectors are disposed in spaced relationship along the axial length of the medical instrument to accurately determine alignment of the medical instrument during the ultrasonic imaging procedure.

The medical instrument on which the ultrasonic reflector is disposed may be an elongate needle. The needle may have opposed proximal and distal ends, with the distal end defining the tip to be inserted into the patient, and the proximal end being secured to a needle hub for mounting the needle on a hypodermic syringe. A lumen may extend axially entirely through the needle to enable extraction of bodily fluid for subsequent diagnostic analysis or to enable injection of an appropriate medication. The needle with the ultrasonic reflector thereon may be used in combination with a stylet extending through the lumen of the needle. The needle and the stylet may be simultaneously inserted into the patient, with the insertion being guided by the ultrasonic signals reflected from the small gaseous bubbles entrained at selected locations along the length of the needle or along the entire length of the needle. Once the needle has reached its specified location, the stylet may be removed from the lumen, and the needle hub may be attached to the mounting collar of a syringe barrel, such that the lumen to the needle is placed in fluid communication with the chamber of the syringe barrel. The syringe may then be used to obtain a tissue sample or to inject the required dose of medication.

DETAILED DESCRIPTION OF THE PREFERRED EMBODIMENT

Figure 1:
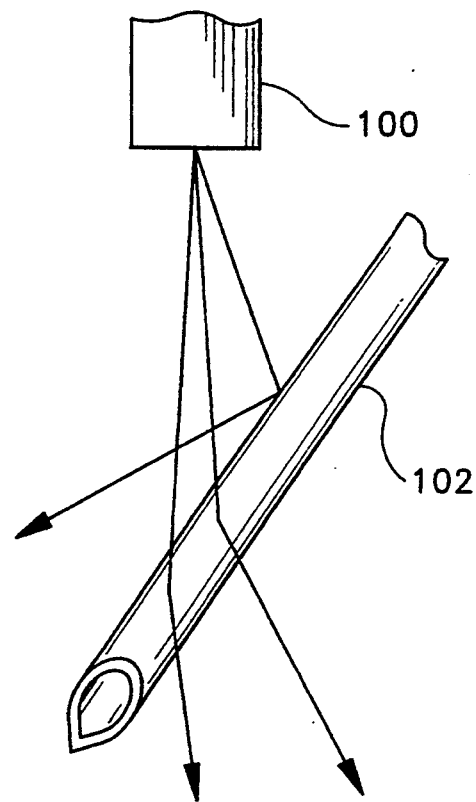
FIG. 1 is a schematic cross-sectional illustration of a transducer for a prior art ultrasonic imaging apparatus and a prior art biopsy needle.
Figure 2:
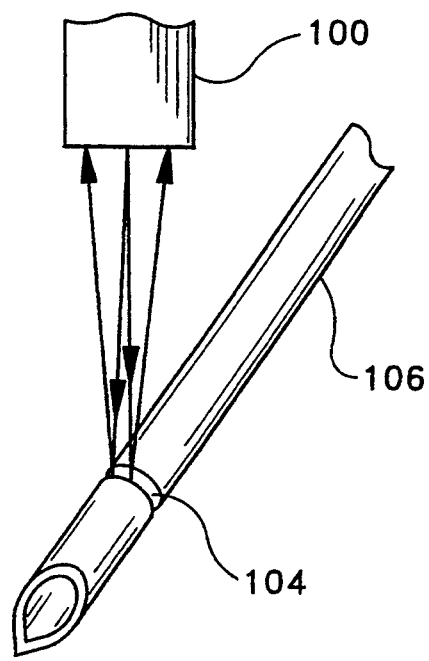
FIG. 2 is a schematic illustration similar to FIG. 1, but showing another prior art biopsy needle.
Figure 3:
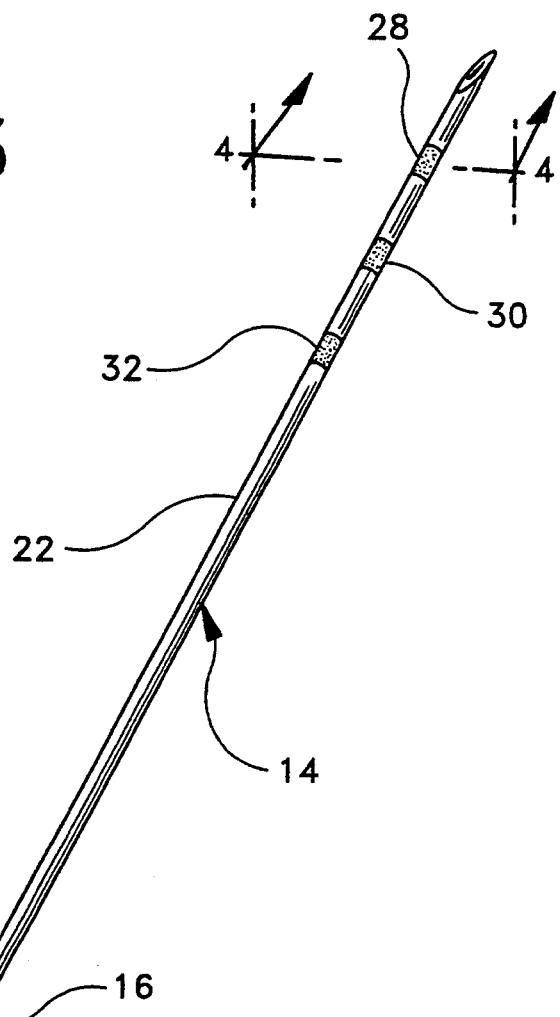
FIG. 3 is a perspective view of a biopsy needle assembly in accordance with the subject invention.
Figure 4:
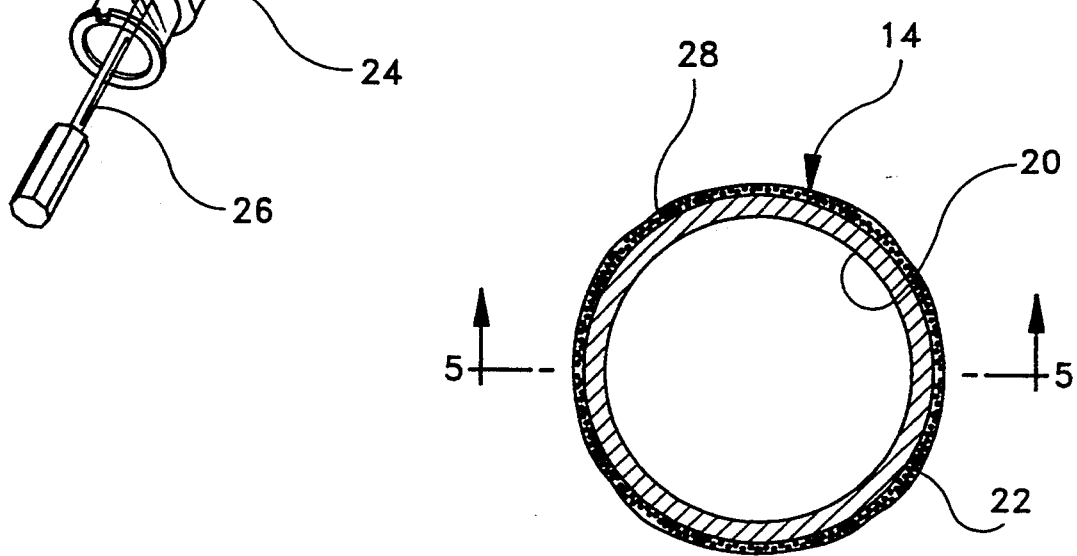
FIG. 4 is a cross-sectional view taken along line 4—4 in FIG. 3.
Figure 5:
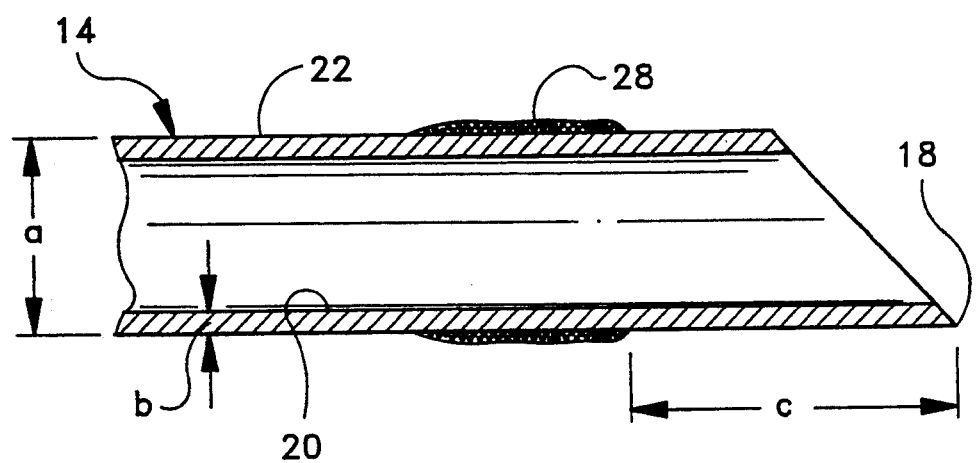
FIG. 5 is a cross-sectional view taken along line 5—5 in FIG. 4.

A needle assembly in accordance with the subject invention identified generally by the numeral 10, is depicted 10 in FIGS. 3–5. Needle assembly 10 includes a biopsy needle 12 having an elongate needle cannula 14. Needle cannula 14 has a proximal end 16, an opposed sharply pointed distal end 18 and a cylindrical lumen 20 extending therebetween as shown in FIGS. 4 and 5. Needle cannula 14 also includes a substantially smooth cylindrical exterior surface 22. As shown in FIG. 5, needle cannula 14 typically will define an outside diameter "a" of about 0.020–0.080 inch and a wall thickness b of about 0.003–0.010 inch. Biopsy needle 12 further includes a mounting hub 24 securely affixed to proximal end 16 of needle cannula 14. Mounting hub 24 is threadedly engageable with a luer collar of hypodermic syringe (not shown).

Biopsy needle assembly 10 includes a stylet 26 slidably and removably disposed within lumen 20 of needle cannula 14. Stylet 26 substantially blocks lumen 20 to prevent distal end 18 of needle cannula 14 from butting a core of tissue during insertion of needle cannula 14 into a patient. Stylet 26 typically will be retained in needle cannula 14 during insertion of needle cannula 14 into a patient. However, stylet 26 may be slidably removed from needle cannula 14 after distal end 18 of needle cannula 14 is properly positioned in the patient. Mounting hub 24 may then be threadedly engaged with a luer collar of a hypodermic syringe.

Biopsy needle 12 is characterized by one or more ultrasonic reflectors 28–32 at axial spaced positions along needle cannula 14. Ultrasonic reflector 28 functions to locate distal end 18 of needle cannula 14 in the video image produced by an ultrasonic imaging apparatus. As a result, ultrasonic reflector 28 is desirably close to distal end 18 and a known distance "c" therefrom. Ultrasonic reflectors 30 and 32 are used to define the alignment of needle cannula 14 on the video monitor of the ultrasonic imaging apparatus. As a result, the precise location and spacing between ultrasonic reflectors 28–32 normally is less critical than the distance "c" between ultrasonic reflector 28 and distal end 18.

As shown most clearly in FIGS. 4 and 5, the ultrasonic reflectors define annular deposits of ultrasonically reflectable material securely disposed on outer circumferential surface 20 of needle cannula 14. Each ultrasonic reflector is preferably a polymeric foam having a matrix of gas bubbles contained therein and sized to maximize the number of reflecting surfaces in the space available. As noted above, air is a good reflector of ultrasonic energy. Furthermore, the large number of spherical air bubbles entrained in each reflector 28–32 provide a large number of surfaces from which the ultrasonic energy may be reflected. Spherically shaped air bubbles are desirable because the spherical surface always presents a reflective facet or surface portion to the observer. Although some of the ultrasonic energy will be reflected away from the transducer of the ultrasonic imaging apparatus, each spherical air bubble significant percentage will be reflected along alignments that will enable detection by the transducer. Smaller bubbles, even microscopic in size, are desirable.

Figure 6:
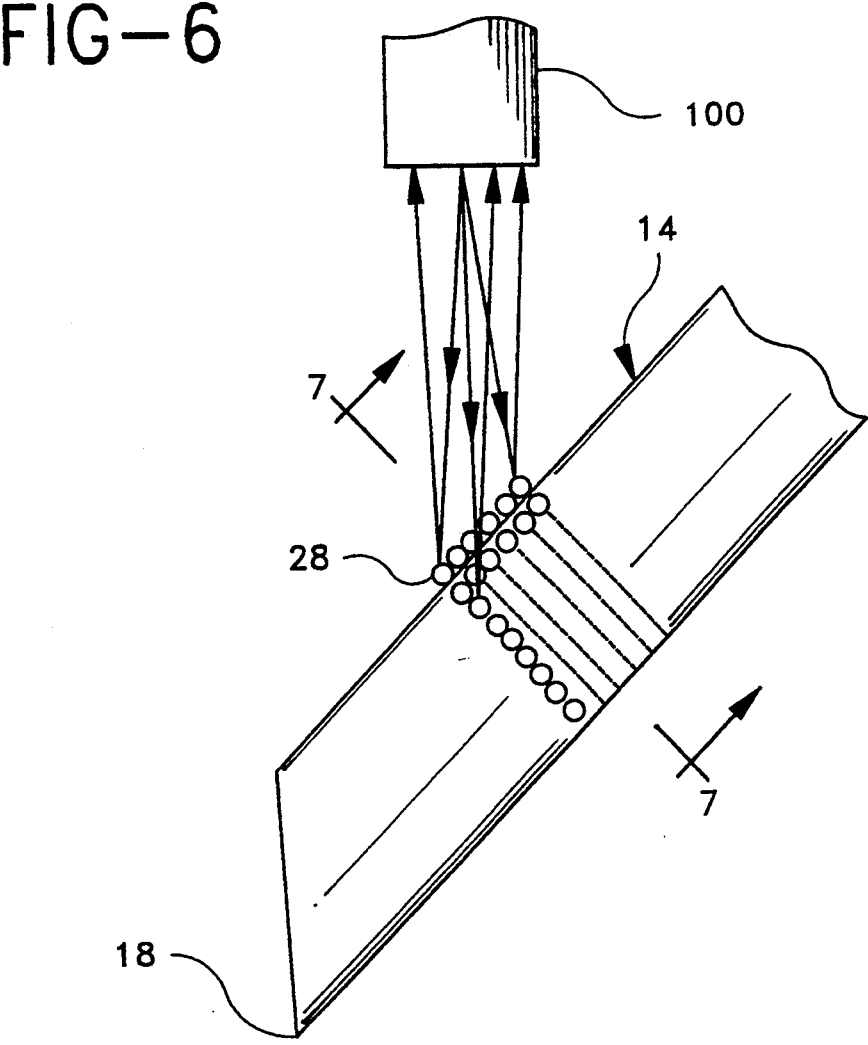
FIG. 6 is a schematic illustration similar to FIGS. 1 and 2, but showing the biopsy needle of FIGS. 3–5.
Figure 7:
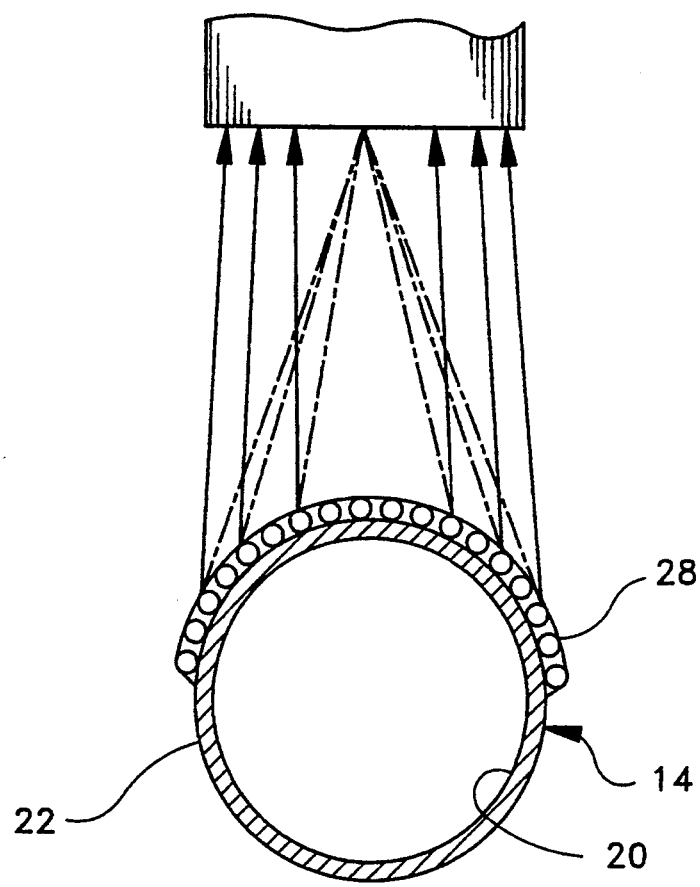
FIG. 7 is a cross-sectional view taken along line 7—7 in FIG. 6.

Regardless of the angle of incidence, virtually all spherical bubbles impinged upon by ultrasonic energy will reflect some of the ultrasonic energy impinging thereon back toward transducer 100, as illustrated schematically in FIGS. 6 and 7. This will result in a circumferentially much wider and axially much longer reflective area than had been available in the prior art. Additionally, ultrasonic energy that is not reflected by the air bubbles will pass through the ultrasonic reflector 28–32 and may be reflected by the underlying needle cannula 14. Thus, ultrasonic reflectors 28–32 effectively add to any ultrasonic reflectivity that may be provided by the underlying portions of the needle cannula 14.

Figure 8:
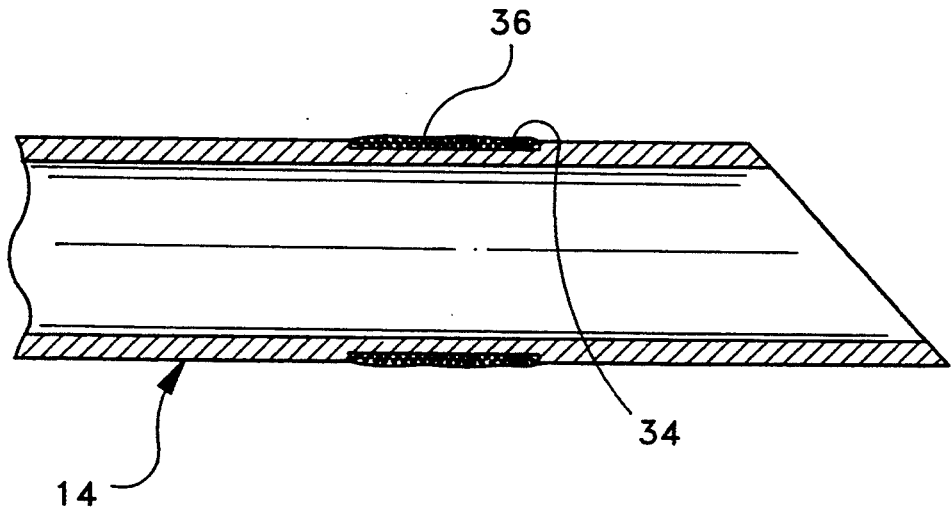
FIG. 8 is a cross-sectional view similar to FIG. 5, but showing an alternate needle embodiment.

The preferred embodiment depicted in FIGS. 4 and 5 includes the polymeric foam material with the matrix of entrained air bubbles deposited directly on the exterior surface 22 of the cylindrical needle cannula 14. This construction will provide a slight cross-sectional discontinuity at axial locations along the needle cannula 14 coinciding with each ultrasonic reflector 28–32. The cross-sectional discontinuity will provide no functional disadvantages for most applications. In this regard, cross-sectional discontinuities are defined by the above described prior art biopsy needles with annular grooves. Applications may exist where a more uniform cross-section is desired. For these applications, as shown in FIG. 8, undercuts 34 are provided in the needle cannula 14' at selected locations. The polymeric foam with the matrix of entrained air bubbles is then deposited in the undercut 34 to define an ultrasonic reflector 36 having an outside diameter approximately equal to the outside diameter "a" of needle cannula 14'. Undercut 34 also defines a region along needle cannula 14' for mechanically anchoring the annular band of polymeric foam which defines the ultrasonic reflector 36.

The technology of making plastic materials having air bubbles, such as foam, is known in the art. Several different methods are used to produce foam parts, these methods or systems disburse a gas into the polymer melt during processing. This is done either by adding a chemical blowing agent to the compound or by inducing a gas directly into the melt. The gas creates the cellular core structure in the part during the molding process.

One way of making the medical instrument of the present invention is to insert mold the ultrasonically reflectable material around the probe or needle cannula. Curable resin, containing gas bubbles, may also be applied to the exterior of the probe or needle cannula.

What is claimed is:

1. A medical instrument for ultrasonic imaging comprising an elongate probe for insertion into a patient and at least one discrete deposit of ultrasonically reflectable material affixed to an exterior surface of the probe, said deposit displaying a substantially smooth outer surface, said ultrasonically reflectable material including a matrix of gas bubbles contained therein for reflecting ultrasonic energy.

2. The medical instrument of claim 1, wherein the ultrasonic reflector is a polymeric foam material having said matrix of gas bubbles contained therein.

3. The medical instrument of claim 1, wherein said gas bubbles contained in said ultrasonic reflector are substantially spherically shaped.

4. The medical instrument of claim 1 wherein said elongate probe has a substantially circularly shaped cross-section.

5. The medical instrument of claim 4, wherein said discrete deposit of ultrasonically reflectable material is substantially annular and is deposited around the exterior surface of said elongate probe.

6. The medical instrument of claim 5, wherein said medical instrument includes an annular undercut extending into the exterior surface region of the elongate probe, said ultrasonically reflectable material being disposed in said annular undercut.

7. The medical instrument of claim 1, comprising a plurality of said ultrasonic reflectors at axial spaced positions along said elgonate probe.

8. The medical instrument of claim 1 wherein said at least one discrete deposit of ultrasonically reflectable material covers most of the exterior surface of said probe.

9. A biopsy needle assembly for ultrasonic imaging said biopsy needle assembly comprising an elongate needle cannula having opposed proximal and distal ends and a lumen extending axially therebetween, and at least one discrete ultrasonic reflector securely affixed to an exterior surface of said needle cannula, said ultrasonic reflector having a substantially smooth outer surface and comprising a matrix of gas bubbles contained therein for reflecting ultrasonic energy impinging on said biopsy needle.

10. The biopsy needle assembly of claim 9, wherein said ultrasonic reflector comprises a polymeric foam.

11. The biopsy needle assembly of claim 9 comprising a plurality of said ultrasonic reflectors at spaced axial positions on said needle cannula.

12. The biopsy needle assembly of claim 9, wherein said gas bubbles contained in said ultrasonic reflector are substantially spherically shaped.

13. The biopsy needle assembly of claim 9, wherein said ultrasonic reflector defines at least one annular band secured circumferentially around said exterior surface of said needle cannula.

14. The biopsy needle assembly of claim 9 further including a stylet slidably and removably disposed within said lumen of said needle cannula.

15. The biopsy needle assembly of claim 9 further including a mounting hub affixed to said proximal end of said needle cannula for mounting said biopsy needle to a hypodermic syringe.

16. The biopsy needle assembly of claim 9 wherein said distal end of said needle cannula includes a sharp cutting edge.

17. The biopsy needle assembly of claim 9 wherein said needle cannula has a substantially circularly shaped cross section.

18. The biopsy needle assembly of claim 9 wherein said needle cannula is made of stainless steel.

19. A medical instrument for ultrasonic imaging comprising an elongate probe for insertion into a patient and at least one discrete deposit of a plastic foam affixed to an exterior surface of the probe, the plastic foam displaying a substantially smooth outer surface and containing therein a matrix of gas bubbles for reflecting ultrasonic energy.

20. A biopsy needle assembly for ultrasonic imaging, the biopsy needle assembly comprising an elongate needle cannula having opposed proximal and distal ends and a lumen extending axially therebetween, and at least one discrete ultrasonic reflector formed of a plastic foam securely affixed to an exterior surface of the needle cannula, the ultrasonic reflector displaying a substantially smooth outer surface and containing therein a matrix of gas bubbles for reflecting ultrasonic energy impinging on the biopsy needle.

* * * * *